United States Patent [19]

Ramsey, III et al.

[11] Patent Number: 4,627,440
[45] Date of Patent: Dec. 9, 1986

[54] SPHYGMOMANOMETRIC CUFF PRESSURIZING SYSTEM

[75] Inventors: Maynard Ramsey, III; James M. Muskatello; Rush W. Hood, Jr., all of Tampa; Richard Medero, Lutz; Stanley K. Stephenson, Tampa, all of Fla.

[73] Assignee: Critikon, Inc., Tampa, Fla.

[21] Appl. No.: 751,835

[22] Filed: Jul. 5, 1985

[51] Int. Cl.⁴ ............................................... A61B 5/02
[52] U.S. Cl. ..................................... 128/682; 128/685
[58] Field of Search ............................... 128/680–686

[56] References Cited

U.S. PATENT DOCUMENTS 4,167,181 9/1979 Lee ....................................... 128/682
4,417,587 11/1983 Ichinomiya et al. ................ 128/682

Primary Examiner—Kyle L. Howell
Assistant Examiner—Francis J. Jaworski
Attorney, Agent, or Firm—Audley A. Ciamporcero, Jr.

[57] ABSTRACT

An inflatable, deflatable cuff, worn by the subject, is coupled to an air reservoir which is at a predetermined pressure which is above systolic pressure. The pressure head is established by a pump mechanism preferably located within the reservoir. When the reservoir is operatively coupled to the cuff, the cuff quickly inflates to a desired artery-occluding initial pressure preparatory to a following blood pressure measuring cycle of operation. The air pump resumes air flow into the reservoir when pressure within the reservoir falls below a predetermined threshold in preparation for a subsequent measurement cycle. The pump also supplies air directly to the cuff should the reservoir contents ever be inadequate to inflate fully the occluding cuff.

19 Claims, 3 Drawing Figures

SPHYGMOMANOMETRIC CUFF PRESSURIZING SYSTEM

FIELD OF THE INVENTION

This invention relates to automated blood pressure monitoring, and more particularly to those classes of automated blood pressure monitors that utilize a pneumatic cuff to exert counterpressure on the vasculature of the subject.

CROSS REFERENCE TO RELATED APPLICATIONS

Reference is hereby made to the following concurrently filed co-pending commonly assigned patent applications: OSCILLOMETRIC BLOOD PRESSURE MONITOR EMPLOYING NON-UNIFORM PRESSURE DECREMENTING STEPS, Ramsey et al., Ser. No. 751,840; IMPROVED AUTOMATED MEAN ARTERIAL BLOOD PRESSURE MONITOR WITH DATA ENHANCEMENT, Ramsey et al., Ser. No. 751,826; IMPROVED AUTOMATED SYSTOLIC BLOOD PRESSURE MONITOR WITH DATA ENHANCEMENT, Ramsey et al., Ser. No. 751,827; IMPROVED AUTOMATED DIASTOLIC BLOOD PRESSURE MONITOR WITH, DATA ENHANCEMENT, Ramsey et al., Ser. No. 751,825.

BACKGROUND OF THE INVENTION

Many automated blood pressure monitors employ an inflatable cuff to exert controlled counterpressure on the vasculature of the subject. One large class of such monitors, exemplified by that described in U.S. Pat. Nos. 4,349,034 and 4,360,029, both to Maynard Ramsey, III and commonly assigned herewith, employs the oscillometric methodology. In accordance with this method, a pneumatic cuff is inflated to a pressure which substantially blocks an artery, such as the brachial artery, and then is progressively relaxed, i.e., stepwise. Heart contractions produce blood pressure pulsations which produce oscillations in blood pressure cuff pressure at the point of occlusion. and the amplitudes of these oscillations are measured and processed to determine mean arterial pressure, systolic pressure, and diastolic pressure.

In some variants of oscillometric systems, the cuff pressure is continuously bled, typically in linear fashion, rather than being relaxed in predetermined decrements. Typically in both, however, cuff pressure is established by a pump mechanism which, under electronic or computer control, is activated at the initiation of the measurement cycle to inflate the cuff. Thereafter, the cuff is deflated with the aid of selectively actuated pressure venting valves. Clearly, such systems place great reliance on the speed, accuracy, and reliability of such a pump. Even the best and fastest commercial pumping apparatus may require in the range of 5-10 seconds for the pump to establish a desired cuff pressure (e.g. 3 to 4 psi) prior to initiation of the depressurization and measurement cycle. In a measurement cycle taking 20-30 seconds by itself, the additional time required for inflation, being non data-productive, constitutes a wasteful interlude.

Instead of inflating initially to above systolic pressure followed by a deflation sequence during which measurements are taken, systems are also known that interrupt the initial rapid inflation at a point below diastolic pressure, with controlled further inflation to above systolic, measurements being taken during the controlled further inflation phase.

It is, accordingly, a primary object of the present invention to reduce the overall blood pressure measurement time by reducing the time required for cuff inflation at the initiation of each cycle.

The proliferation of apparatus available in the critical care unit, intensive care unit, or operating theatre has placed a premium on space. It is, therefore, desirable either to minimize the space occupied by blood pressure apparatus, or at the least, while functionally improving the monitors, to avoid increasing the space allocation necessary for the monitors. Likewise, portability of monitors suggests reduction of the overall size of the apparatus.

It is therefore another object of the present invention to provide accelerated inflation while maintaining or decreasing the overall size of the monitor. It is a further object to provide compact, effective inflation apparatus with a reduced power, accuracy, and speed burden on the pump.

Another disadvantage found in presently available automatic monitoring apparatus of the foregoing type is the disturbing noise level produced by the air pump when operating. Therefore, it is yet another object of the present invention to produce an apparatus wherein the noise produced by the pump is substantially confined within the apparatus.

SUMMARY OF THE INVENTION

In accordance with the principles of the present invention, when measurements are to be taken during cuff deflation, a reservoir is maintained with a pressure head above the systolic blood pressure of a subject, and is coupled to the cuff at the initiation of the measurement cycle. Pressurized air from the reservoir very rapidly pressurizes the cuff to initially occlude for an entire heart cycle the subject's artery experiencing the cuff pressure. Thereafter, valve mechanisms associated with the cuff are utilized controllably to reduce the cuff pressure, either continuously or decrementally, as desired. Further, as a back-up to the reservoir, the pump is connected directly to the cuff to ensure adequate pressure for accurate sphygmomanometric measurements. When measurements are to be taken during cuff inflation, initial rapid cuff pressurization is to a lower level usually below diastolic.

In a preferred embodiment, the pump is located within the reservoir, communicating with the ambient atmosphere through openings in the housing which defines the reservoir. This efficiently utilizes scarce space within the composite blood pressure measuring unit; and also mutes the sounds of the energized pump.

BRIEF DESCRIPTION OF THE DRAWINGS

The invention will be better understood after reading the following detailed description of the presently preferred embodiments thereof with reference to the appended drawings in which.

The same reference numerals are used throughout the drawings to designate the same or similar parts.

DETAILED DESCRIPTION OF THE PRESENTLY PREFERRED EMBODIMENTS

Reference should be had to U.S. Pat. No. 4,360,029 to Ramsey which discloses in great detail a system for oscillometric blood pressure monitoring to which the principles of the present invention may be applied with advantage. The disclosure of the Ramsey '029 patent is incorporated by reference herein.

Figure 1:
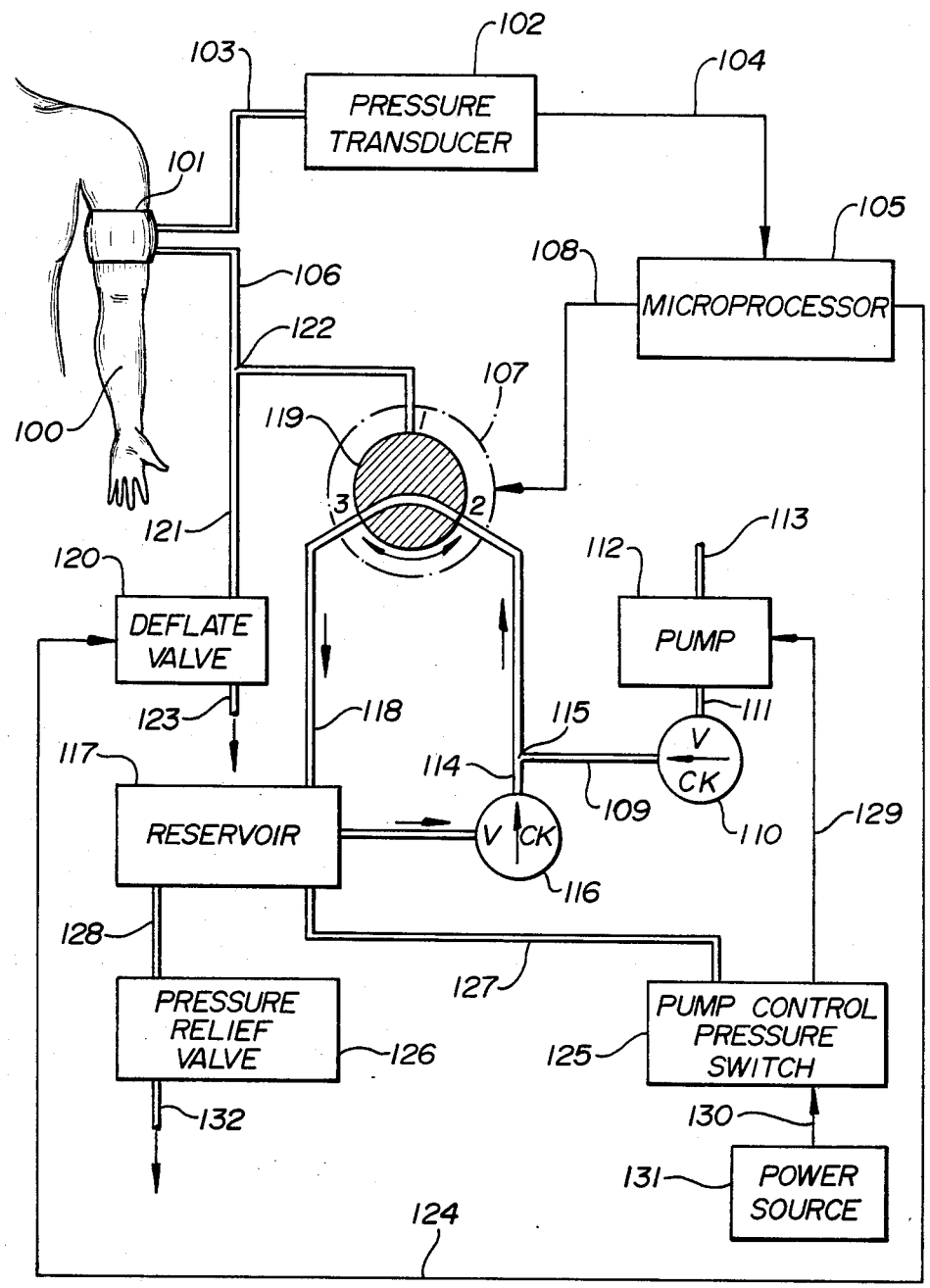
FIG. 1 is a schematic representation of a system and the basic components embodying the present invention.

Referring to FIG. 1 herein, there is shown an illustrative embodiment of the principles of the present invention. The arm 100 of a human subject is shown wearing a conventional flexible inflatable and deflatable cuff 101 for occluding the brachial artery when fully relieved. A pressure transducer 102 is coupled by a duct 103 to the cuff 101 and senses the pressure obtaining therein. In accordance with conventional oscillometric techniques, pressure oscillations in the artery are sensed by changes in the counterpressure of the cuff 101, and in turn by the transducer 102, there to be converted to an electrical signal and coupled over path 104 to a microprocessor or other controller 105. From the standpoint of the principles of the present invention, the processing of the signals from pressure transducer 102 by the microprocessor 105 to produce blood pressure data, and optionally to reject artifact data, can be conducted in accordance with the prior art, for example in accordance with the teachings of the above-referenced Ramsey '029 patent.

Alternatively, the blood pressure can be determined in accordance with the teachings of M. Ramsey, III et al, in their concurrently filed patent application entitled "Method of Automated Blood Pressure Detection", U.S. Pat. No. 4,543,962 dated Oct. 1, 1985, commonly assigned herewith, the disclosure of which is incorporated herein by reference.

The cuff 101 is also shown coupled by a duct 106 to a first port, designated by the numeral "1", of a multiposition valve 107. The valve 107 is electrically controlled through a connection 108 from the microprocessor 105. Valve 107 has two other ports, designated "2" and "3", respectively, port number "2" being connected by a duct 109 through a check valve 110 to the output 111 of a pneumatic pump 112. The pump 112 has an inlet 113 communicating with the atmosphere. A branch duct 114 also communicates with port "2" of valve 107 through a junction at 115 with the duct 109. The other end of duct 114 communicates through a check valve 116 with the interior of a reservoir 117. The interior of the reservoir is also placed in direct communication by a duct 118 with the third port of the valve 107. As shown in the drawing, valve 107 has an actuator member 119 which interconnects, in the position illustrated. the ports "2" and "3". The valve is arranged when actuated, e.g., rotated counterclockwise 120°, to interrupt the connection to port "3" and place ports "1" and "2" in communication.

The deflate valve apparatus 120 is connected by duct 121 to a branch connection at 122 with the duct 106 leading from cuff 101. An exhaust connection from deflate valve apparatus 120 is shown at 123. The valve apparatus 120 receives electrical control over a path 124 from the microprocessor 105. Pressurized air within reservoir 117 is supervised by a pump control pressure switch 125 and a pressure relief valve 126, the former being connected to the reservoir 117 by a duct 127 while the latter is connected to the reservoir 117 by a duct 128. In this illustrative embodiment the pump control pressure switch 125 is shown connected electrically over a path 129 to the pump 112 and over a path 130 to a power source 131. Pressure relief valve 126 is illustrated provided with a vent output 132. However, valve 126 may be any suitable blow-out plug or the like known to the art.

Referring now to the operation of the apparatus illustrated in FIG. 1, when the power is first turned on, air pressure in the reservoir 117 is approximately atmospheric. Consequently, the pump control pressure switch 125, which is pressure sensitive, will be in condition to complete a circuit for activating pump 112 from the power source 131 over paths 129 and 130. The switch 125 has a low level operating threshold above the highest systolic pressure that the apparatus is intended to measure, usually above 6–10 p.s.i. At present, the low level point is preferably about 6–8 p.s.i. Upon activation, pump 112 will force air from its inlet 113 to its outlet 111 and then through the check valve 110, duct 109, valve 107 (in the position shown in the drawing) and duct 118 to the interior of reservoir 117. This pumping action will continue until the pump control pressure switch 125 senses through duct 127 that the pressure within reservoir 117 has reached a predetermined upper level preset value above the low level threshold, e.g., between 8 and 10 p.s.i. At present, about 8 p.s.i. is preferred. When this occurs, the pressure switch 125 will disrupt the energization of pump 112 over paths 129 and 130.

When it is desired to initiate a determination of blood pressure, the microprocessor 105 furnishes a signal over path 108 to the valve 107 (valve 107 may be referred to as an inflate valve) to cause valve member 119 to rotate so as to interconnect ports "1" and "2". Two paths now can be traced through valve 107. The first path is from reservoir 117 through check valve 116, duct 114, valve 107 and duct 106 to the cuff 101. The second path is from the pump outlet 111 through the check valve 110, duct 109, and valve 107 to duct 106 and cuff 101. It is assumed that the deflate valve apparatus 120 is closed.

Assuming a typical adult cuff of approximately one half liter volume, and assuming a reservoir 117 with a volume of approximately one half liter to one liter, i.e., between one and two times the volume of the cuff, pressurized to 8 p.s.i., upon actuation of valve 107 the pressurized air in reservoir 117 will tend to discharge into cuff 101 until pressure equilibrium is attained. Based upon volume considerations of the reservoir, cuff and interconnections, and ignoring the augmentation provided by the connection to the outlet 111 of the pump 112, the system will equilibrate to a pressure in the range of 3 to 4 p.s.i. This assumes no further control from the microprocessor 105. However, it is preferred that the microprocessor 105 respond to the signal from the pressure transducer 102, indicative of the instantaneous pressure in the cuff 101, to interrupt the inflation of the cuff 101 when the pressure in the cuff reaches a predetermined value generally above systolic pressure. Such interruption will be accomplished by feeding a signal over path 108 to restore valve 107 to the position shown in FIG. 1, insulating the cuff 101 from its two sources of inflation, the reservoir 117 and the pump 112. Of course, if a different measurement sequence is adopted, the initial pressure at which inflation is interrupted can be below diastolic or at any other desired level.

If for any reason the pressure in reservoir 117 drops below that in cuff 101 prior to the pressure in cuff 101 reaching the desired level, check valve 116 will close permitting the pump 112 through its check valve 110 to increase cuff pressure until the desired pressure in cuff 101 is reached. It is assumed that the reservoir pressure has dropped below that which calls for energizing pump 112, e.g., below 6 p.s.i.

During the inflation of the cuff 101, the pressure in the reservoir 117 will begin to drop since the reservoir 117 has been disconnected from the pump and the pressurized air therein is being used to inflate cuff 101. As soon as the pressure within reservoir 117 drops below the low level threshold for pressure switch 125, (i.e., 6 p.s.i.) the latter will reenergize pump 112. It should be understood that until pump 112 is reenergized, the check valve 110 will prevent the pressurized air coming from reservoir 117 through check valve 116 from flowing backwards through the pump 112.

As soon as the inflate valve 107 is closed to the cuff 101 and assumes the position shown in FIG. 1, the pump 112 will resume supplying air to reservoir 117 if the pressure in the reservoir has dropped below the preset threshold level. This pressurizing of reservoir 117 can take place simultaneously with actuation of the deflate valve apparatus 120 under control of the microprocessor 105 to measure the subject's blood pressure.

The construction is such that the pump can relatively slowly pressurize the reservoir 117 which, when the latter is connected to the cuff 101, will rapidly inflate the cuff. Actual measurement of the blood pressure under the control of the microprocessor 105 and the deflate valve apparatus 120 and as sensed by pressure transducer 102 can be accomplished in any suitable manner such as that disclosed in said Ramsey, III patents or said Ramsey, III et al. patent application. At the completion of each measurement cycle, the deflate valve apparatus 120 can be reopened long enough to relax the cuff pressure substantially completely. Thereafter, the deflate valve apparatus 120 can be closed pending a new measurement cycle.

Figure 2:
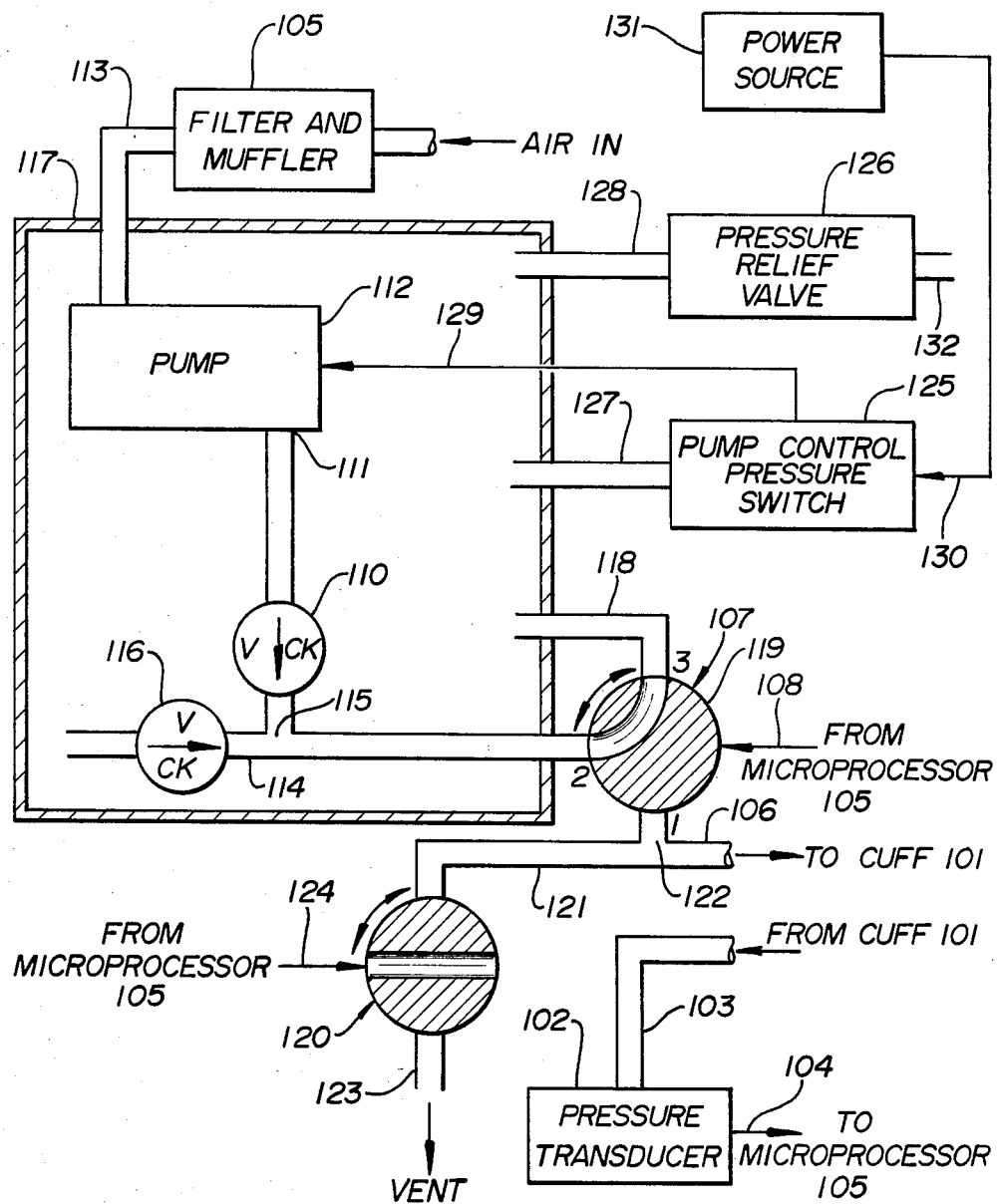
FIG. 2 is a quasi diagrammatic-schematic illustration of a preferred embodiment wherein the pump is located within the reservoir.

As shown in FIG. 1, the various components of the system are separately located. In particular, the reservoir 117 is shown standing alone. However, considerable advantage can be obtained by locating the pump within the reservoir 117 as shown in FIG. 2 to which attention should now be directed. The advantage of locating the pump within the reservoir is twofold. First, it provides a convenient way of soundproofing to isolate the users of the equipment from the normal noise generated by the pump. Secondly, locating the pump within the reservoir achieves a significant economy of space since space tends to be at a premium where the subject blood pressure measuring equipment is generally used.

Although not illustrated in FIG. 1, a filter and muffler 150 may be connected, as shown in FIG. 2, in the air inlet 113 to the pump 112. Because the operation and construction of the various components in FIG. 2, except for their relative location, are essentially the same as that in FIG. 1, the various components bear the same reference numerals. This will facilitate an understanding of the operation of the equipment.

By way of summation, during pressure generation, if the reservoir pressure drops below the lower set pressure. e.g., below 6 p.s.i., the pump will be turned on and will subsequently be turned off when the reservoir pressure reaches the upper set pressure, e.g., 8 p.s.i. When a blood pressure measurement is desired, the inflate valve will be opened while the cuff pressure is supervised until the cuff pressure reaches the desired level at which time the inflate valve will be closed. Thereafter, the deflate valve apparatus is opened and the measurement taken. This may be accomplished in stepwise fashion or in any other desired manner. Alternatively, the blood pressure determination can take place during stepped or continuous inflation of the cuff pressure above some quickly attained level with the deflate valve dumping the air from the cuff at the end of the measurement cycle.

Figure 3:
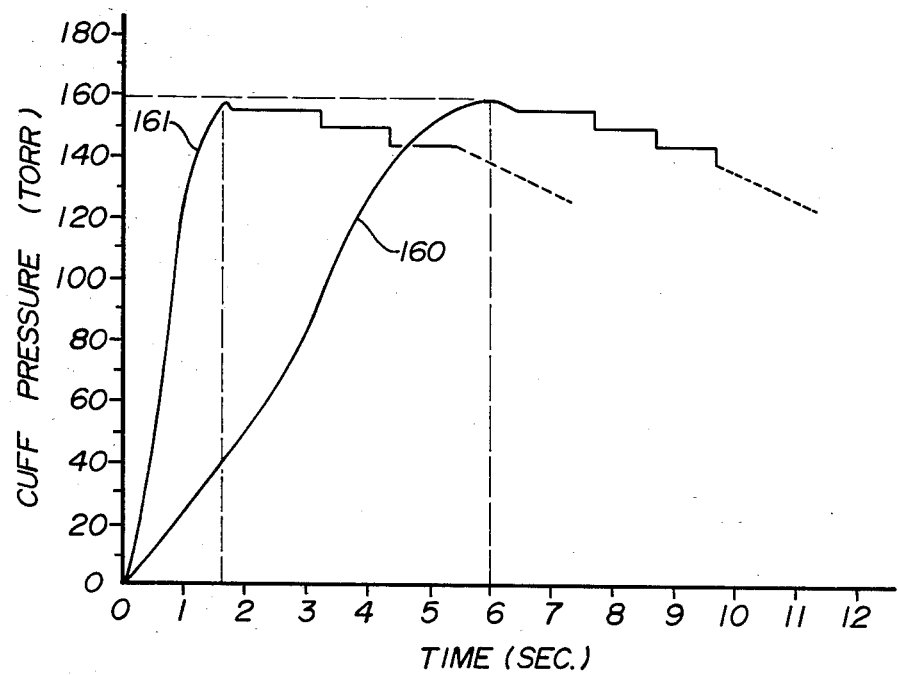
FIG. 3 is a pressure versus time graph comparing the operation of a prior art system with the operation of the present invention.

Reference should now be had to FIG. 3 which graphically illustrates the substantial advantage obtained through use of the present invention. There is depicted therein a first plot, designated 160, of cuff pressure versus time illustrating the time it takes, approximately 6 seconds, to inflate a cuff to the normal occlusion pressure of approximately 160 torr employing known prior art apparatus relying upon direct inflation from the pump. By contrast, when the reservoir arrangement of the present invention is employed to rapidly inflate the cuff, normal occlusion pressure in the cuff is reached in less that 2 seconds as illustrated by curve 161 in FIG. 3. Of course, it will be understood that a higher initial pressure may be required when taking measurements from a subject with high blood pressure.

Referring again to FIGS. 1 and 2, it will be understood that the pressure relief valve 126 is furnished as a safety device to ensure that the pressure within reservoir 117 will not reach dangerous levels if pump control switch 125 (or any other aspect of the energizing circuit for the pump 112) should malfunction for any reason. The valve 126 can be set to vent reservoir 117 through outlet 132 whenever the pressure in reservoir 117 reaches the valve set point at a suitable level above the upper level setting of pump switch 125.

In a presently preferred embodiment, the pump 112 may be a Model 5002 pump commercially available from ASF. Many other commercially available pumps are also suitable for the apparatus. The inflate valve 107, as well as deflate valve apparatus 120, may be implemented by Model E2012 valves commercially available from Precision Dynamics, Inc., of New Britain, Conn. It should be apparent that other comparable valves are commercially available from other sources, however, such valves should be fast acting.

The pump control pressure switch 125 can be a Model MPL601 switch, available from Micro Pneumatics Logic, Inc. Any suitable pressure relief valve can be used for the valve 126.

Summarizing, the principles of the present invention in their broadest form involve establishment of cuff pressure based on use of a pre-pressurized reservoir with a direct pump connection as back-up. In addition, the invention involves enclosing the pump within the reservoir structure both for soundproofing and space economy. It should also be understood, that various of the other components such as the valves and/or pressure switches can be incorporated within the confines of the reservoir 117, if desired.

It should also be apparent that the multi-position valve 107 may be thought of as providing separate valve means, i.e., one valve means involving ports "2" and "3", for interconnecting the pump 112 with the interior of the reservoir 117, and another valve means involving ports "1" and "2", for interconnecting the reservoir 117 with the cuff 101. Additionally, the check valves 110 and 116 provide valve means for establishing, via valve 107, direct communication between pump 112 and cuff 101. Those skilled in the art will appreciate that the multiple functions of valve 107 could be accomplished with separate two-port valves.

While control of the pump 112 in the illustrative embodiments of the invention described above has been accomplished using the pressure switch 125, it is contemplated that pump operation can be under the control of the microprocessor in which case a pressure transducer responsive to reservoir pressure will furnish signals to the microprocessor which, in turn, will control suitable power switching components between the power source 131 and the pump 112.

The example described above deals with an adult pressure cuff. These cuffs come generally in four different sizes. In addition there are neonatal cuffs of much smaller sizes. With the pump pressure switch 125 operative between 6 and 8 p.s.i., and with a reservoir having a volume approximately equal to that of an adult cuff, the reservoir pressure will fall below 6 p.s.i. before the cuff pressure attains its desired level. The pump will become energized and will assist further inflation of the cuff. If the pressure in the cuff becomes at least equal to the reservoir pressure and it is desired to increase the cuff pressure, it will be appreciated that the check valve 116 will close directing all of the pump output to the cuff and none to the reservoir until the inflate valve closes. The situation is different with a small volume neonatal cuff. Now the reservoir volume is many times larger than the cuff volume, and pressurization of the cuff to its desired level will be accomplished before the reservoir 117 drops its internal pressure below the threshold value of 6 p.s.i. Consequently, the pump is not called into direct action until after several inflate cycles.

It will be appreciated that the foregoing has set forth the presently preferred and illustrative embodiments of the principles of the present invention, but that numerous alternative embodiments will occur to those skilled in the subject art without departure from the true spirit or scope of the invention as defined in the appended claims.

What is claimed is:

1. Blood pressure measuring apparatus comprising:
   (a) an inflatable and deflatable pressure cuff;
   (b) means defining a pneumatic reservoir;
   (c) a pneumatic pump located within said reservoir means, including air inlet means coupling said pump to the exterior of said reservoir means;
   (d) first valve means interconnecting said pump and the interior of said reservoir means for selectably supplying air under pressure from said pump to said reservoir means to pressurize said reservoir means;
   (e) second valve means interconnecting said reservoir means and said cuff for selectably establishing air transfer communication between said reservoir means and said cuff to cause a rapid inflation of said cuff;
   (f) means coupled to said cuff for sensing cuff pressure;
   (g) deflate valve means coupled to said cuff for releasing air from said cuff; and
   (h) means coupled to said first and second valve means for controlling the operation thereof to inflate said cuff upon initiation of a blood pressure measuring cycle.

2. Blood pressure measuring apparatus according to claim 1, wherein said first and second valve means are constituted by a single multi-position valve mechanism having a first position for coupling an outlet of said pump to the interior of said reservoir means, and having a second position for coupling said reservoir means to said cuff.

3. Blood pressure measuring apparatus according to claim 2, wherein said interconnection of said pump said reservoir means, and said multi-position valve mechanism is such that said pump outlet is coupled in direct communication with said cuff when said multi-position valve mechanism is in said second position.

4. Blood pressure measuring apparatus according to claim 3, wherein said multi-position valve mechanism comprises first, second and third ports and a valve member for selectably establishing communication between said first and second ports or between said second and third ports, a first duct connecting said first port with said cuff, a second duct connecting said pump outlet through a check valve to said second port, a third duct connecting said third port to the interior of said reservoir means, and a further duct including a check valve connecting said second port to said interior of said reservoir means.

5. Blood pressure measuring apparatus according to claim 4, wherein said check valves are located within said reservoir means.

6. Blood pressure measuring apparatus according to claim 5, further comprising means for sensing the air pressure within said reservoir means, and pump control means interconnecting said last mentioned means and said pump for causing operation of said pump when the pressure within said reservoir means falls below a first preset level above the highest systolic pressure that the apparatus is intended to measure.

7. Blood pressure measuring apparatus according to claim 6, wherein said first preset level is above 6 p.s.i.

8. Blood pressure measuring apparatus according to claim 7, wherein said pump control means is constructed and arranged to interrupt operation of said pump when the pressure within said reservoir means reaches a second preset level above said first preset level.

9. Blood pressure measuring apparatus according to claim 8, wherein said second preset level is within the range of 8 to 10 p.s.i.

10. Blood pressure measuring apparatus according to claim 1, further comprising means for sensing the air pressure within said reservoir means, and pump control means for interconnecting said last mentioned means and said pump causing operation of said pump when the pressure within said reservoir means falls below a first preset level above the highest systolic pressure that the apparatus is intended to measure.

11. Blood pressure measuring apparatus according to claim 10, wherein said first preset level is above 6 p.s.i.

12. Blood pressure measuring apparatus according to claim 11, wherein said pump control means is constructed and arranged to interrupt operation of said pump when the pressure within said reservoir means reaches a second preset level above said first preset level.

13. Blood pressure measuring apparatus according to claim 12, wherein said second preset level is within the range of 8 to 10 p.s.i.

14. Blood pressure measuring apparatus according to claim 1, wherein said reservoir means has a volume at least as large as the volume of said cuff.

15. Blood pressure measuring apparatus according to claim 14, wherein said reservoir means has a volume substantially between one and two times the volume of said cuff.

16. Blood pressure measuring apparatus comprising:
    (a) an inflatable and deflatable pressure cuff;
    (b) means defining a pneumatic reservoir;
    (c) a pneumatic pump;
    (d) first valve means interconnecting said pump and the interior of said reservoir means for selectably supplying air under pressure from said pump to said reservoir means to pressurize said reservoir means;
    (e) second valve means interconnecting said reservoir means and said cuff for selectably establishing air transfer communication between said reservoir means and said cuff to cause a rapid inflation of said cuff;
    (f) means coupled to said cuff for sensing cuff pressure;
    (g) deflate valve means coupled to said cuff for releasing air from said cuff; and
    (h) means coupled to said first and second valve means for controlling the operation thereof to inflate said cuff upon initiation of a blood pressure measuring cycle,
    (i) wherein said first and second valve means are constituted by a single multi-position valve mechanism having a first position for coupling an outlet of said pump to the interior of said reservoir means, and having a second position for coupling said reservoir means to said cuff.

17. Blood pressure measuring apparatus according to claim 16, wherein said interconnection of said pump, said reservoir means, and said multi-position valve mechanism is such that said pump outlet is coupled in direct communication with said cuff when said multi-position valve mechanism is in said second position.

18. Blood pressure measuring apparatus according to claim 17, wherein said multi-position valve mechanism comprises first, second and third ports and a valve member for selectably establishing communication between said first and second ports or between said second and third ports, a first duct connecting said first port with said cuff, a second duct connecting said pump outlet through a check valve to said second port, a third duct connecting said third port to the interior of said reservoir means, and a further duct including a check valve connecting said second port to said interior of said reservoir means.

19. Blood pressure measuring apparatus comprising:
    (a) an inflatable and deflatable pressure cuff;
    (b) means defining a pneumatic reservoir;
    (c) a pneumatic pump;
    (d) first valve means interconnecting said pump and the interior of said reservoir means for selectably supplying air under pressure from said pump to said reservoir means to pressurize said reservoir means;
    (e) second valve means interconnecting said reservoir means and said cuff for selectably establishing air transfer communication between said reservoir means and said cuff to cause a rapid inflation of said cuff;
    (f) means coupled to said cuff for sensing cuff pressure;
    (g) deflate valve means coupled to said cuff for releasing air from said cuff;
    (h) means coupled to said first and second valve means for controlling the operation thereof to inflate said cuff upon initiation of a blood pressure measuring cycle; and
    (i) a third valve means interconnecting said pump and said cuff for selectably establishing direct air transfer communication between said pump and said cuff during the period of cuff inflation to ensure full cuff inflation whenever the contents of said reservoir means is insufficient.

* * * * *